(12) United States Patent
Cole et al.

(10) Patent No.: US 6,553,995 B1
(45) Date of Patent: Apr. 29, 2003

(54) KIT FOR SUPPORT AND STABILIZATION OF SURGICAL PATIENT EXTREMITIES

(76) Inventors: Peter Alexander Cole, 123 Carriage La., Madison, MS (US) 39110; Douglas Eric Parsell, 327 Arlington Cir., Ridgeland, MS (US) 38157

( * ) Notice: Subject to any disclaimer, the term of this patent is extended or adjusted under 35 U.S.C. 154(b) by 0 days.

(21) Appl. No.: 09/685,812

(22) Filed: Oct. 10, 2000

(51) Int. Cl.$^7$ ............................................... A61F 13/00
(52) U.S. Cl. ............................... 128/846; 5/648; 5/650
(58) Field of Search ................................ 128/845, 846, 128/869, 882; 602/5, 23; 5/648, 649, 650, 651

(56) References Cited

U.S. PATENT DOCUMENTS

| | | | |
|---|---|---|---|
| 3,762,404 A | 10/1973 | Sakita | |
| 3,873,081 A | 3/1975 | Smith | |
| 4,136,858 A | 1/1979 | Peterson | |
| 4,194,601 A | * 3/1980 | Yellin | ............................ 190/2 |
| 4,218,792 A | 8/1980 | Cogan | |
| 4,481,943 A | 11/1984 | Michalson | |
| 4,620,698 A | 11/1986 | Reed | |
| 4,681,309 A | 7/1987 | Lechner | |
| 4,742,981 A | 5/1988 | Converse | |
| 4,745,647 A | 5/1988 | Goodwin | |
| 4,836,523 A | 6/1989 | Englander | |
| 4,863,788 A | * 9/1989 | Bellairs | ....................... 428/246 |
| 5,014,375 A | 5/1991 | Coonrad | |
| 5,016,268 A | 5/1991 | Lotman | |
| 5,125,123 A | * 6/1992 | Engle | ............................ 5/648 |
| 5,289,828 A | * 3/1994 | Toth | ............................ 128/845 |
| 5,369,825 A | 12/1994 | Reesby | |
| 5,462,551 A | 10/1995 | Bailey | |
| 5,645,079 A | 7/1997 | Zahiri | |
| 5,754,997 A | 5/1998 | Lussi | |
| 5,775,334 A | 7/1998 | Lamb | |
| 5,809,597 A | * 9/1998 | Shaw | ............................ 5/644 |
| 5,819,743 A | 10/1998 | McMillan | |
| 5,906,205 A | 5/1999 | Hiebert | |
| 6,032,669 A | * 3/2000 | Klein | ............................ 5/650 |

OTHER PUBLICATIONS

AliMed, Operating Room and Diagnostic Imaging Products, 1998–1999, p. C34–C35, 297 High Street, Dedham, MA, USA.

* cited by examiner

*Primary Examiner*—Michael A. Brown
(74) *Attorney, Agent, or Firm*—Workman, Nydegger & Seeley

(57) ABSTRACT

The patient positioning kit described herein is a set of vinyl-coated polyurethane foam forms and storage unit. The kit functions to support injured patient extremities during specific surgical procedures. The kit may be tailored to certain surgical specialties such as orthopedic traumatology or orthopedic sports medicine. For the given surgical specialty, each kit is composed of foam forms specifically for the most often performed surgical procedures within that specialty. Each kit contains a significant variety of support pieces such that various patient sizes and extremity positions may be stabilized. Both arm and leg associated procedures are facilitated by component pieces of the patient positioning kit. The kit pieces are coated with a polymeric material that forms a protective shell that increases piece durability and reduces fluid uptake.

21 Claims, 3 Drawing Sheets

KIT FOR SUPPORT AND STABILIZATION OF SURGICAL PATIENT EXTREMITIES

BACKGROUND OF THE INVENTION

1. The Field of the Invention

The invention disclosed herein is in the field of human limb positioning, more particularly the field of surgical patient extremity positioning. More particularly, the invention is in the field of kits designed for stabilizing surgical patient extremities during specific orthopedic surgical procedures via procedure specific coated foam forms.

2. The Relevant Technology

During the coarse of executing many surgical procedures, more specifically, orthopaedic procedures, it is helpful to hold an unconscious patient's arm or leg in a specific position. Traditionally, this has been accomplished by constructing custom extremity supports from coiled up surgical towels, surgical blankets, surgical sheets and sterile adhesive tape. Inherent problems with this approach include time-consuming construction, consumption of costly supplies, instability, lack of reproducibility and a tendency for structural deterioration during long procedures.

In an attempt to provide more efficient support of patient extremities during surgical procedures, two basic classes of devices have evolved; mechanically adjustable devices and non-adjustable foam devices.

Of the mechanically-based devices, devices may be further delineated as adjustable surgical tables (U.S. Pat. No. 5,369,825, Reesby 1994), frames that attach to the surgical table (U.S. Pat. No. 4,481,943 Michelson 1984, U.S. Pat. No. 4,836,523 Englander 1989, U.S. Pat. No. 4,742,981 Converse 1988) or mechanical, electrical and/or hydraulic mechanisms that hold an extremity (U.S. Pat. No. 5,645,079 Zahiri 1997, U.S. Pat. No. 4,620,698 Reed 1986, U.S. Pat. No. 4,136,858 Peterson 1979, U.S. Pat. No. 5,775,334 Lamb 1998, U.S. Pat. No. 5,462,551 Bailey 1995, U.S. Pat. No. 4,681,309 Lechner 1987).

Of the non-mechanical devices, devices may be further delineated as whole body supports for blood flow control, patient comfort, ease of x-ray cassette insertion and the like (U.S. Pat. No. 4,745,647 Goodwin 1988, U.S. Pat. No. 5,016,268 Lotman 1991, U.S. Pat. No. 5,014,375 Coonrad 1991, U.S. Pat. No. 3,873,081 Smith 1975, U.S. Pat. No. 5,754,997 Lussi 1998) non-mechanical extremity.supports for non-surgical applications (U.S. Pat. No. 4,218,792 Kogan 1980, U.S. Pat. No. 5,819,743 McMillin 1998) and shape-conforming "bean-bags" (U.S. Pat. No. 3,762,404 Sakita 1973, U.S. Pat. No. 5,906,205 Hiebert 1999).

There currently exists a void amongst the mechanical and non-mechanical devices for surgical stabilization of patient extremities. While the mechanical devices offer adequate stability and control, they are technically difficult to utilize, require significantly long set-up times, are relatively expensive and are not readily mobile from one operating table to another. On the other hand, the non-mechanical devices provide adequate patient comfort but in general, fail to directly address extremity stabilization and support. The devices that do address extremity support (Kogan 1980 and McMillin 1998) are not designed for the facilitation of surgical procedures but rather for individual user comfort.

There exists commercially available products, such as the Protecta-Coat Positioners from AliMed Inc., Dedham, Mass. USA, that offer a range of coated, foam blocks which are suitable for patient positioning during surgery. The shapes are of general utility but do not specifically address the extremity positioning requirements of specific orthopaedic trauma procedures. The shapes are of one size for each design, therefore, not affording a close fit for a wide size range of patients. The individual pieces are presented as single unit devices as opposed to a well-coordinated kit of pieces designed to cover a range of specific orthopaedic surgical procedures. The presently available commercial products also fail to make available a means for convenient and orderly storage of the individual coated foam pieces.

BRIEF SUMMARY AND OBJECTS OF THE INVENTION

The orthopedic trauma positioning kit of the present discussion consists of a set of polymer-coated foam shapes which when taken together yield a comprehensive device for extremity positioning during orthopedic trauma surgical procedures. The kit consists of all the pieces required for the positioning of all extremities for a wide size range of patients and for all commonly required orthopedic trauma upper and lower extremity surgical procedures. The kit is housed in a multi-sided storage structure to facilitate organization of the individual pieces and to minimize the required storage space. The combination of multi-sized, polymer-coated foam shapes specific for given surgical procedures housed in a custom storage system constitutes the orthopedic trauma positioning kit.

BRIEF DESCRIPTION OF SEVERAL VIEWS OF THE DRAWINGS

The following drawings depict only a typical embodiment of the invention and are not therefore to be considered to be limiting of its scope, the invention will be described and explained with the additional specificity and detail through the use of the accompanying drawings in which.

DETAILED DESCRIPTION OF THE INVENTION

There exists a need for a system of devices to provide efficient and effective extremity stabilization for orthopedic trauma surgical procedures. Previous attempts to meet these needs have focussed on cumbersome, expensive, mechanical devices or non-procedure specific soft-sided shapes and wedges.

The orthopedic trauma positioning kit described herein is unique in its ability to comfortably position and stabilize variable sized patients' extremities for all commonly performed orthopedic trauma surgeries. An essential component of the orthopedic trauma positioning kit is a storage device for the set of patient positioning shapes. This storage device allows for clean storage of the individual kit pieces between surgical procedures, accurate inventorying of kit pieces and efficient conservation of operating room floor space.

In its preferred embodiment, the individual pieces that constitute the orthopedic trauma positioning kit are composed of a polyurethane foam material that is coated with a durable vinyl layer. The stiffness of the foam material may be altered through the control of filler content within the foam. The texture of the foam may also be altered through incorporation of rubber-like polymeric elements into the urethane structure. Alterations in the mechanical properties of the utilized foam may be needed to tailor a given piece's mechanical properties to that which would be ideal for the surgical application. Examples of required mechanical responses from foam pieces includes adequate stiffness for shaped which bridge one of the patient's extremities or adequate softness and compressibility for shapes which contact pressure sensitive area of the patient's body for long time periods during surgical procedures. The shape of each individual polyurethane foam piece may be produced through an industrially common cutting or casting process.

The individual kit pieces are coated with a vinyl layer to enhance durability, prevent fluid uptake, facilitate disinfection, enhance non-slip surfaces and allow for esthetic coloration of the pieces. Blends of Teflon containing vinyls may also be used for this purpose; The coating may be applied through an industrially common spray or dipping process.

Figure 1:
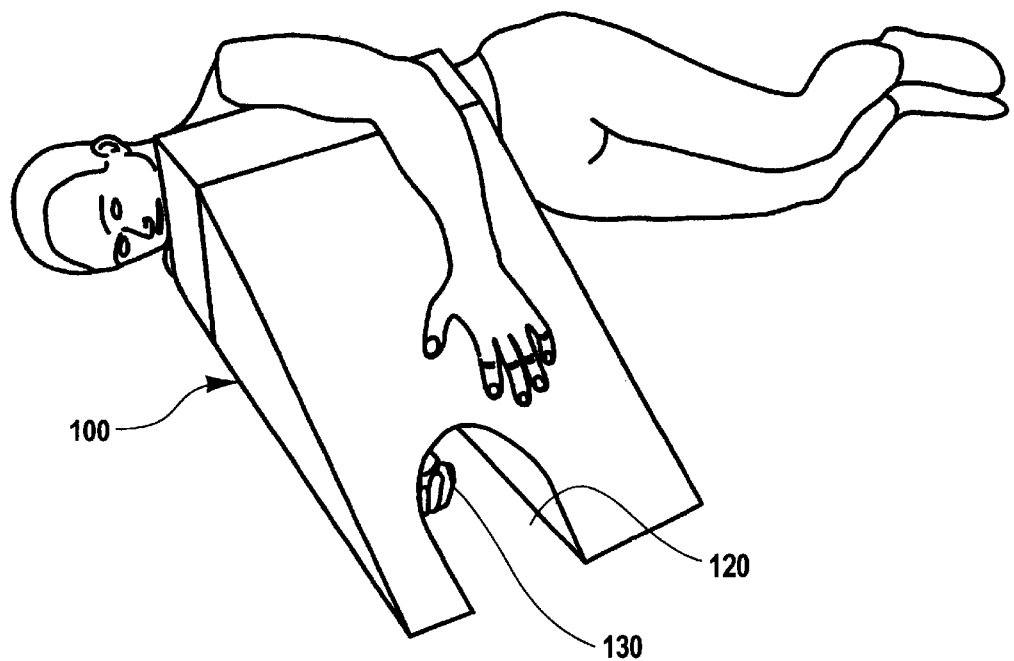
FIG. 1 is a typical arm support triangle with the associated width adjustment block as it could be used clinically.
Figure 2:
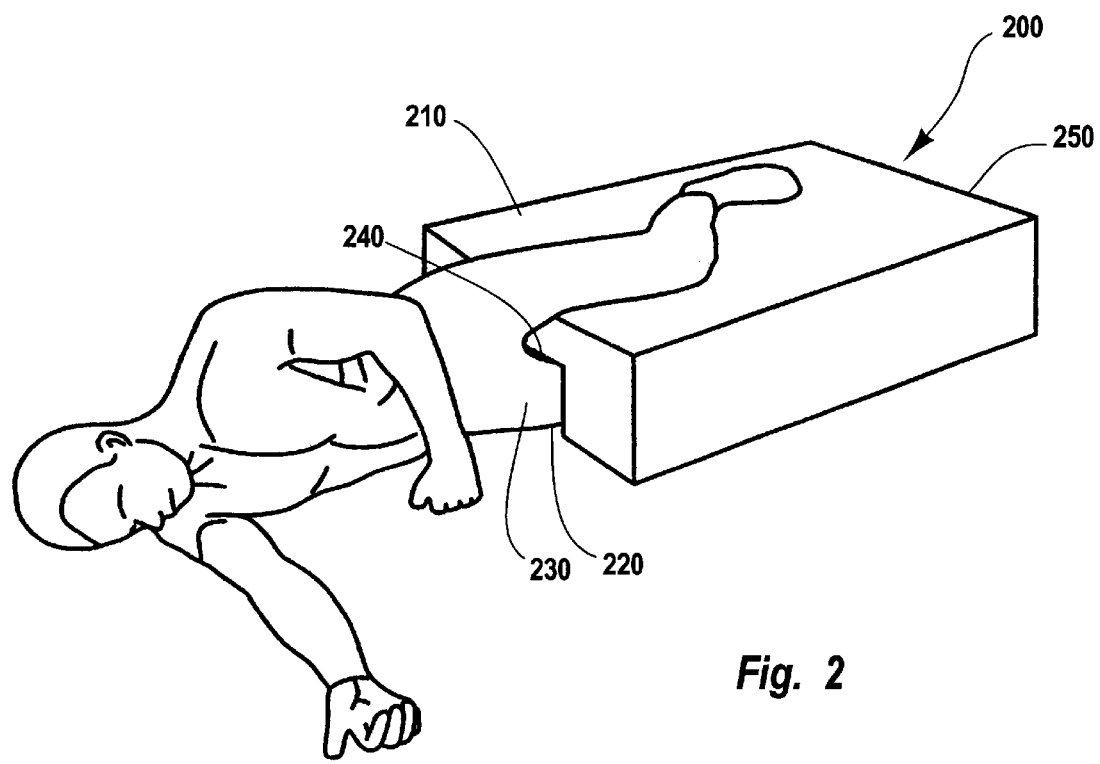
FIG. 2 is an upper leg support for stabilizing a patient's leg while the patient is positioned on their side and provide a working surface for the surgeon.
Figure 3:
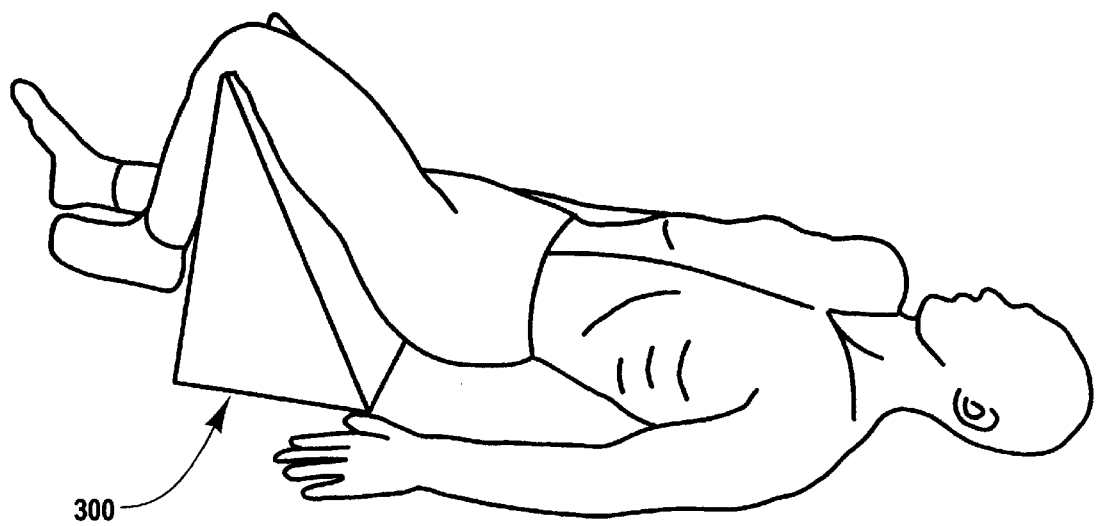
FIG. 3 is a typical leg support triangle as it could be used clinically.
Figure 4:
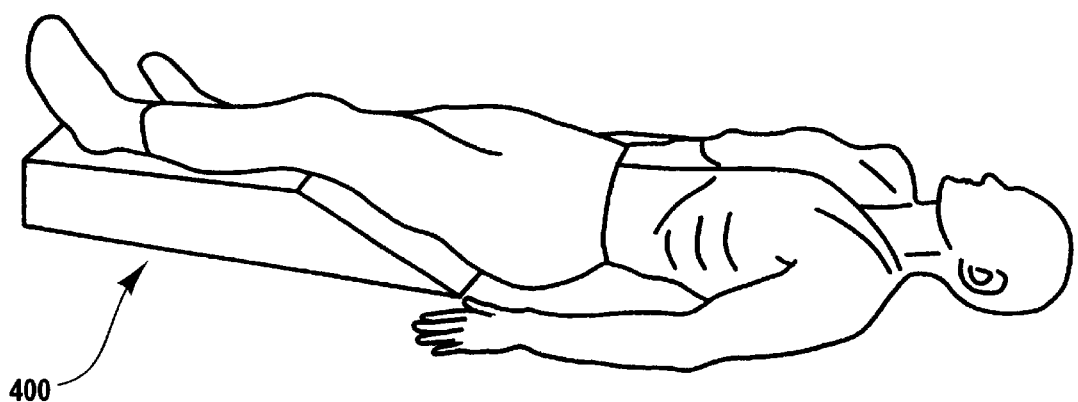
FIG. 4 is a typical leg elevator support as it could be used clinically.

A typical orthopedic trauma positioning kit would consist of right and left arm wedges in large and small sizes for arm positioning for orthopedic procedures such as open reduction internal fixation of fractures of the supracondylar-intracondylar humerus, olecranon and both bones of the forearm. FIG. 1 shows a possible clinical usage of the orthopedic arm wedge 100. The uninjured arm 130 is shown passing through the arm wedge 100 via a tunnel 120. Easy access to the uninjured arm 130 is especially useful for administration of i.v. lines during the surgical procedure. Said kit may also contain right and left leg tunnel pieces to facilitate stabilization of the patient in a position of lying on their side while the orthopedic surgeon performs open reduction internal fixation of fractures of the foot and ankle, in particular the calcaneus. FIG. 2 shows a possible clinical usage of the leg tunnel kit piece 200. The cavity 220 whereby the uninjured leg 230 passes underneath the top surface 210 of the piece 200 can be open at both ends 240, 250 of the piece 200. This feature allows for viewing and if needed positioning of the uninjured foot and/or leg 230. Said kit may also contain large and small acute angle triangular pieces for intramedullary nailing of the tibia. FIG. 3 shows a possible clinical usage of such a triangular piece 300. Said kit may also contain large and small triangular pieces of less acute angulation than the previously described piece for utilization during retrograde femoral nailing, knee ligament reconstruction and open reduction internal fixation of the distal femur or tibial shaft. Said kit may also contain a leg elevator for open reduction internal fixation for fractures of the patella, ankle, tibial pilon, talas, midfoot, forefoot and tibia/fibia shaft fractures. FIG. 4 shows a possible clinical usage of the leg elevator 400. Said kit may also contain a plurality of cylindrical pieces for diverse extremity support requirements.

Figure 5:
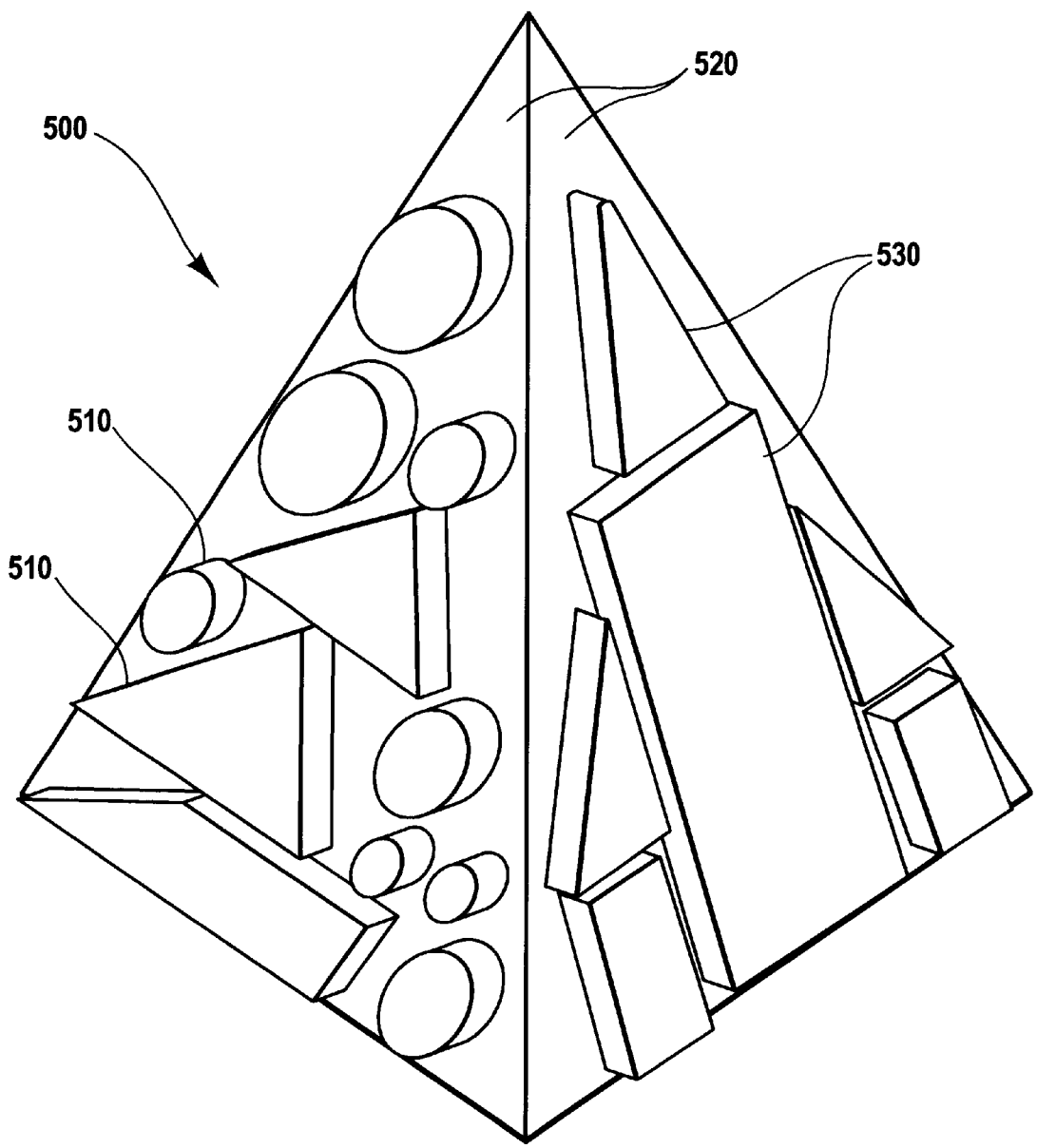
FIG. 5 is a typical orthopedic trauma positioning kit housed by a three-sided storage body.

As previously mentioned, the orthopedic trauma patient positioning kit is composed of a set of individual vinyl-coated polyurethane foam pieces and a storage unit for the entire set of pieces. The storage unit is essential for the practical utilization of the system within the confines of a modern surgical facility. In a preferred embodiment, the storage unit is in the shape of a three-sided pyramid with insets on all three sides to hold each of the kit pieces. FIG. 5 shows a possible configuration of the patient positioning kit when housed within a three-sided pyramidal storage unit 500. The storage unit 500 may be made from various materials such as aluminum alloys, steel alloys, plastics, composites, acrylics, polyurethane foam or vinyl-coated polyurethane foam. The indentations 510 for each kit piece within the exterior surfaces 520 of the storage unit are of a depth such that when kit pieces 530 are inserted they protrude sufficiently to allow for easy removal but express sufficient retention forces to prevent accidental dislodgment.

The present invention may be embodied in other specific forms without departing from its spirit or essential characteristics. The described embodiments are to be considered in all respects only as illustrative and not restrictive. The scope of the invention is, therefore, indicated by the presented claims as opposed to the previous description. All changes which come within the meaning and range of equivalency of the claims are to be embraced within their scope.

What is claimed and desired to be secured by the United States Letters Patent is:

1. An orthopedic surgical support kit for providing stable positioning of patient limbs during surgery, the kit comprising:

a first flexible support structure that is sized and configured so as to provide a support surface for at least one of a patient's ankle, wrist or knee during an orthopedic surgical procedure; and one or more additional flexible support structures sized and configured so as to provide a support surface for at least one of an ankle, wrist or knee during an orthopedic surgical procedure, at least one of the additional flexible support structures being of a different size or shape than the first flexible support structure, at least one of the flexible support structures comprising a flexible foam material coated with a polymeric layer.

2. An orthopedic surgical support kit as defined in claim 1, wherein at least one of the additional flexible support structures is of the same shape but of different size compared to the first flexible support member so that the first flexible support structure provides a support surface for a joint of a first patient and at least one additional flexible support structure provides a support surface for a similar joint in a differently sized patient.

3. An orthopedic surgical support kit as defined in claim 1, wherein at least one of the additional flexible support structures is of a different shape compared to the first flexible support member so that the first flexible support structure provides a support surface for a first joint of a patient and at least one additional flexible support structure provides a support surface for a different joint.

4. An orthopedic surgical support kit as defined in claimed 1, wherein at least one of the flexible support structures is sized and configured so as to provide a support surface for an ankle of a patient.

5. An orthopedic surgical support kit as defined in claim 1, wherein at least one of the flexible support structures is sized and configured so as to provide a support surface for a wrist of a patient.

6. An orthopedic surgical support kit as defined in claim 1, wherein at least one of the flexible support structures is sized and configured so as to provide a support surface for a knee of a patient that is lying on his or her back.

7. An orthopedic surgical support kit as defined in claim 6, at least one of the flexible support structures including an inclined section adapted to raise a patient's thigh at an incline when the patient is lying on his or her back and a horizontal section adapted to support the remaining portion of the patient's leg in a substantially horizontal orientation.

8. An orthopedic surgical support kit as defined in claim 1, at least one of the flexible support structures having a circular, elliptical or triangular cross section.

9. An orthopedic surgical support kit as defined in claim 1, at least one of the flexible support structures having a rectangular cross section.

10. An orthopedic surgical support kit as defined in claim 1, the flexible foam material comprising a polyurethane foam.

11. An orthopedic surgical support kit as defined in claim 10, the polyurethane foam comprising at least one of a filler or a rubber-like polymeric element.

12. An orthopedic surgical support kit as defined in claim 1, the polymeric layer comprising a vinyl polymer.

13. An orthopedic surgical support kit as defined in claim 12, the vinyl polymer comprising a blend of a vinyl polymer and tetrafluorethylene.

14. An orthopedic surgical support kit as defined in claim 1, the kit comprising at least one flexible support member that is adapted to provide support for at least one portion of a patient's body other than or in addition to an ankle, wrist or knee.

15. An orthopedic surgical support kit as defined in claim 1, further comprising a storage unit that includes a plurality of indentations, each of which is adapted to receive therein a different one of the flexible support members.

16. An orthopedic surgical support kit for providing stable positioning of patient limbs during surgery, the kit comprising:
   a first support structure comprising a flexible foam material coated with a polymeric layer, the first support structure being sized and configured so as to provide a support surface for at least one of a patient's ankle, wrist or knee during an orthopedic surgical procedure; and
   one or more additional support structures comprising a flexible foam material coated with a polymeric layer and being sized and configured so as to provide a support surface for at least one of an ankle, wrist or knee during an orthopedic surgical procedure, at least one of the additional support structures being of a different size or shape than the first support structure.

17. An orthopedic surgical support kit as defined in claim 16, wherein at least one of the support structures is sized and configured so as to provide a support surface for an ankle of a patient.

18. An orthopedic surgical support kit as defined in claim 16, wherein at least one of the support structures is sized and configured so as to provide a support surface for a wrist of a patient.

19. An orthopedic surgical support kit for providing stable positioning of patient limbs during surgery, the kit comprising:
   a first flexible support structure comprising a flexible foam material coated with a polymeric layer, the first flexible support structure being sized and configured so as to provide a support surface for at least one of a patient's ankle, wrist or knee during an orthopedic surgical procedure;
   one or more additional flexible support structures comprising a flexible foam material coated with a polymeric layer and being sized and configured so as to provide a support surface for at least one of an ankle, wrist or knee during an orthopedic surgical procedure, at least one of the additional flexible support structures being of a different size or shape than the first flexible support structure; and
   a storage unit that includes a plurality of indentations, each of which is adapted to receive therein a different one of the flexible support members.

20. An orthopedic surgical support kit for providing stable positioning of patient limbs during surgery, the kit comprising:
   a first flexible support structure that is sized and configured so as to provide a support surface for at least one of a patient's ankle, wrist or knee during an orthopedic surgical procedure;
   one or more additional flexible support structures sized and configured so as to provide a support surface for at least one of an ankle, wrist or knee during an orthopedic surgical procedure, at least one of the additional flexible support structures being of a different size or shape than the first flexible support structure; and
   a storage unit that includes a plurality of indentations, each of which is adapted to receive therein a different one of the flexible support members.

21. An orthopedic surgical support kit for providing stable positioning of patient limbs during surgery, the kit comprising:
   a first flexible support structure that is sized and configured so as to provide a support surface for at least one of a patient's ankle, wrist or knee during an orthopedic surgical procedure; and
   one or more additional flexible support structures sized and configured so as to provide a support surface for at least one of an ankle, wrist or knee during an orthopedic surgical procedure, at least one of the additional flexible support structures being of a different size or shape than the first flexible support structure,
   at least one of the flexible support structures including an inclined section adapted to raise a patient's thigh at an incline when the patient is lying on his or her back and a horizontal section adapted to support the remaining portion of the patient's leg in a substantially horizontal orientation.

* * * * *